(12) United States Patent
Carrino et al.

(10) Patent No.: US 9,945,855 B2
(45) Date of Patent: Apr. 17, 2018

(54) METHOD FOR LINKING POINT OF CARE RAPID DIAGNOSTIC TESTING RESULTS TO LABORATORY-BASED METHODS

(75) Inventors: John J. Carrino, San Diego, CA (US); James Fan, Carlsbad, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/810,948

(22) PCT Filed: Jul. 20, 2011

(86) PCT No.: PCT/US2011/044674
§ 371 (c)(1),
(2), (4) Date: Feb. 8, 2013

(87) PCT Pub. No.: WO2012/012527
PCT Pub. Date: Jan. 26, 2012

(65) Prior Publication Data
US 2013/0216998 A1 Aug. 22, 2013

Related U.S. Application Data

(60) Provisional application No. 61/366,076, filed on Jul. 20, 2010.

(51) Int. Cl.
*G01N 33/569* (2006.01)
*C12Q 1/68* (2018.01)
*C12Q 1/70* (2006.01)

(52) U.S. Cl.
CPC ..... *G01N 33/56983* (2013.01); *C12Q 1/6806* (2013.01); *C12Q 1/70* (2013.01)

(58) Field of Classification Search
CPC ...... C12Q 1/6825; C12Q 1/686; C12Q 1/689; C12Q 1/6806; C12Q 1/6895; C12Q 2563/143; C12Q 2565/633; C12Q 1/6827; C12Q 1/6834; C12Q 1/70; C12Q 2527/125; C12Q 1/701; C12Q 2527/107; C12Q 2527/15; C12Q 2537/125; C12Q 2547/101; C12Q 2549/101; C12Q 2563/131; C12Q 2565/518; C12Q 2565/607; C12Q 1/6804; C12Q 1/6816; C12Q 1/6818; C12Q 1/6848; C12Q 1/6853; C12Q 1/6876; C12Q 1/6883; C12Q 1/6888; C12Q 2522/101; C12Q 2525/107; C12Q 2525/161; C12Q 2525/301; C12Q 2527/101; C12Q 2545/101; C12Q 2561/113; C12Q 2563/113; C12Q 2563/137; C12Q 2565/101; C12Q 2565/519; C12Q 2565/625; C12Q 1/001; C12Q 1/04; C12Q 1/28; C12Q 1/40; C12Q 1/485; C12Q 1/66; C12Q 1/6809; C12Q 1/6837; C12Q 1/6858; C12Q 1/6881; C12Q 1/688
See application file for complete search history.

(56) References Cited

U.S. PATENT DOCUMENTS

| 3,890,203 | A | * | 6/1975 | Mehl | 600/577 |
|---|---|---|---|---|---|
| 3,901,765 | A | * | 8/1975 | Mehl | 435/34 |
| 3,904,482 | A | * | 9/1975 | Mehl | 435/34 |
| 4,618,576 | A | * | 10/1986 | Rosenstein et al. | 435/7.34 |
| 4,693,972 | A | * | 9/1987 | Mansour et al. | 435/34 |
| 5,084,005 | A | * | 1/1992 | Kachigian | 604/1 |
| 5,091,316 | A | * | 2/1992 | Monthony et al. | 600/572 |
| 5,776,694 | A | * | 7/1998 | Sheiness et al. | 435/6.15 |
| 6,267,722 | B1 | * | 7/2001 | Anderson | G01N 21/474 435/4 |
| 6,394,952 | B1 | * | 5/2002 | Anderson | G01N 21/474 435/4 |

(Continued)

FOREIGN PATENT DOCUMENTS

| EP | 0143329 A2 | 6/1985 |
|---|---|---|
| JP | 08-506421 A | 7/1996 |

(Continued)

OTHER PUBLICATIONS

Liao RS, Tomalty LL, Majury A, Zoutman DE. Comparison of viral isolation and multiplex real-time reverse transcription-PCR for confirmation of respiratory syncytial virus and influenza virus detection by antigen immunoassays. J Clin Microbiol. Mar. 2009;47(3):527-32. Epub Jan. 7, 2009.*
MAGNA Pure Compact RNA Isolation Kit. Package Insert. Roche. Version Printed Nov. 2005.*
MAGNA Pure LC RNA Isolation Tissue Lysis Buffer. Package Insert. Roche. Version 1. Printed Jun. 2003.*
MAGNA Pure LC RNA Isolation Tissue Lysis Buffer. Package Insert. Roche. Version Printed Jun. 2004.*
Beck ET, Jurgens LA, Kehl SC, Bose ME, Patitucci T, LaGue E, Darga P,Wilkinson K, Witt LM, Fan J, He J, Kumar S, Henrickson KJ. J Mol Diagn. Jan. 2010;12(1):74-81. Epub Dec. 3, 2009.*

(Continued)

*Primary Examiner* — Brian J Gangle
(74) *Attorney, Agent, or Firm* — Botos Churchill IP Law LLP

(57) ABSTRACT

A method for using a single sample suspected of containing a microorganism for both a local rapid test immunoassay and a remote laboratory test. The sample is collected from a patient at a physician's office or from the environment to be tested. The sample is collected using a swab or other implement, combined with a rapid test processing reagent and a portion of the processed sample is used for the local rapid test. The rapid test processing reagent typically consists of a buffer, a salt, and a detergent and is compatible with the local rapid test immunoassay. Only a portion of the processed sample is used for the local rapid test, leaving a remaining portion of the processed sample to be used in a remote laboratory assay. At least some of the remaining portion of the processed sample is combined with a stabilization agent that preserves at least the nucleic acid in the processed sample for the remote laboratory assay.

18 Claims, 6 Drawing Sheets

(56) References Cited

U.S. PATENT DOCUMENTS

| | | | |
|---|---|---|---|
| 6,617,170 B2* | 9/2003 | Augello et al. | 436/176 |
| 6,964,752 B2* | 11/2005 | Lappe | B01L 3/502 422/119 |
| 7,662,562 B2* | 2/2010 | Hellyer et al. | 435/6.12 |
| D655,424 S* | 3/2012 | Castanon et al. | D24/225 |
| 8,420,320 B2* | 4/2013 | Hellyer et al. | 435/6.11 |
| 8,603,769 B2* | 12/2013 | Feng et al. | 435/30 |
| 2002/0146677 A1* | 10/2002 | Augello et al. | 435/2 |
| 2004/0176705 A1* | 9/2004 | Stevens et al. | 600/584 |
| 2006/0014302 A1* | 1/2006 | Martinez | G01N 21/474 436/518 |
| 2006/0127924 A1* | 6/2006 | Hellyer et al. | 435/6 |
| 2006/0246423 A1 | 11/2006 | Adelson et al. | |
| 2006/0286557 A1* | 12/2006 | Basehore | C12P 19/34 435/6.14 |
| 2008/0196517 A1* | 8/2008 | Harvey et al. | 73/864.91 |
| 2008/0280296 A1* | 11/2008 | Chen et al. | 435/6 |
| 2009/0098527 A1* | 4/2009 | Fischer et al. | 435/5 |
| 2009/0123909 A1* | 5/2009 | Pourmand et al. | 435/5 |
| 2009/0233309 A1* | 9/2009 | Fischer et al. | 435/6 |
| 2009/0291449 A1 | 11/2009 | Knapp, Jr. et al. | |
| 2009/0306230 A1 | 12/2009 | Semikhodskii et al. | |
| 2009/0312285 A1* | 12/2009 | Fischer et al. | 514/75 |
| 2010/0009343 A1* | 1/2010 | Fischer et al. | 435/5 |
| 2010/0311607 A1* | 12/2010 | Hellyer et al. | 506/9 |
| 2011/0065108 A1* | 3/2011 | Sherman | C12Q 1/6806 435/6.15 |
| 2012/0003710 A1* | 1/2012 | Leinweber et al. | 435/176 |
| 2013/0089886 A1* | 4/2013 | Feng et al. | 435/30 |
| 2014/0329705 A1* | 11/2014 | Wong et al. | 506/9 |

FOREIGN PATENT DOCUMENTS

| | | |
|---|---|---|
| JP | 2004534731 A | 11/2004 |
| JP | 2006084351 A | 3/2006 |
| JP | 2008-164403 | 7/2008 |
| JP | 2009-523458 A | 6/2009 |
| WO | 2004078233 A2 | 9/2004 |
| WO | 2007098184 A2 | 8/2007 |
| WO | WO 2008/096225 A2 | 8/2008 |
| WO | 2010064628 A1 | 6/2010 |

OTHER PUBLICATIONS

Das A, Spackman E, Senne D, Pedersen J, Suarez DL. Development of an internal positive control for rapid diagnosis of avian influenza virus infections by real-time reverse transcription-PCR with lyophilized reagents. J Clin Microbiol. Sep. 2006;44(9):3065-73.*

RNeasy Mini Kit. Protocol Handbook. Qiagen. Jun. 2001.*

SUPERSCRIPT III One-Step RT-PCR System. Kit Handbook. Invitrogen, Feb. 1, 2001.*

Qiu X, Mauk MG, Chen D, Liu C, Bau HH. A large volume, portable, real-time PCR reactor. Lab Chip. Nov. 21, 2010;10(22):31707. Epub Oct. 6, 2010.*

Luo X, Hsing IM. Electrochemical techniques on sequence-specific PCR amplicon detection for point-of-care applications. Analyst. Oct. 2009;134(10):1957-64. Epub Aug. 18, 2009.*

Neuzil P, Novak L, Pipper J, Lee S, Ng LF, Zhang C. Rapid detection of viral RNA by a pocket-size real-time PCR system. Lab Chip. Oct. 7, 2010;10(19):2632-4. Epub Jul. 30, 2010.*

Fearon M. The laboratory diagnosis of HIV infections. Can J Infect Dis Med Microbiol. Jan. 2005;16(1):26-30.*

Gulliksen A, et. al. Towards a "Sample-In, Answer-Out" Point-of-Care Platform for Nucleic Acid Extraction and Amplification: Using an HPV E6/E7 mRNA Model System. J Oncol. 2012;2012:905024. Epub Dec. 22, 2011.*

Jiang J, Park NJ, Hu S, Wong DT. A universal pre-analytic solution for concurrent stabilization of salivary proteins, RNA and DNA at ambient temperature. Arch Oral Biol. Mar. 2009;54(3):268-73. Epub Nov. 28, 2008.*

Charles PG. Early diagnosis of lower respiratory tract infections (point-of-care tests). Curr Opin Pulm Med. May 2008;14(3):176-82.*

Bonner AB, Monroe KW, Talley LI, Klasner AE, Kimberlin DW. Impact of the rapid diagnosis of influenza on physician decision-making and patient management in the pediatric emergency department: results of a randomized, prospective, controlled trial. Pediatrics. Aug. 2003;112(2):363-7.*

Bisoffi Z, Sirima SB, Menten J, Pattaro C, Angheben A, Gobbi F, Tinto H, Lodesani C, Neya B, Gobbo M, Van den Ende J. Accuracy of a rapid diagnostic test on the diagnosis of malaria infection and of malaria-attributable fever during low and high transmission season in Burkina Faso. Malar J. Jul. 7, 2010;9:192.*

Qiagen ALLPREP® DNA/RNA/Protein Mini Handbook, updated Dec. 2014, First available Dec. 15, 2005; https://www.qiagen.com/resources/download.aspx?id=58d2f796-181a-49df-8718-8057e370014d&lang=en.*

ThermoFischer Scientific. "Cell Lysis Solutions." Protein Biology Resource Library. https://www.thermofisher.com/us/en/home/life-science/protein-biology/protein-biology-learning-center/protein-biology-resource-library/pierce-protein-methods/cell-lysis-solutions.html. May 21, 2009.*

Communicable Diseases Network Australian (CDNA) ("Influenza Laboratory Case Definition (LCD)." Jun. 28, 2010. http://www.health.gov.au/internet/main/publishing.nsf/Content/cda-phlncd-influenza.htm.*

Liu H, Gan Y, Wu Y, Weng H, Lei P, Shen G. Effects of different lysis buffers of nucleic acid purification kit on the stability of influenza virus RNA. Future Virology 2014 9:6, 549-555.*

"Thermo Scientific Pierce Cell Lysis Technical Handbook: Featuring Cell Lysis Reagents and Detergents." Thermo Scientific. 2009. Vers.2. https://tools.thermofisher.com/content/sfs/brochures/1601757-Cell-Lysis-Handbook.pdf.*

Nina T. Holland et al, "Biological sample collect ion and processing for molecular epidemiological studies", Mutation Research, 2003, vol. 543, No. 3, pp. 217-234.

International Search Report for Application No. PCT/US2011/044674 dated Apr. 6, 2012.

Extended European Search Report for Application No. 11810337.3 dated Nov. 15, 2013.

Foo H et al: "Laboratory test performance in young adults during influenza outbreaks at World Youth Day 2008", Journal of Clinical Virology. Elsevier, Amsterdam. NL., vo 1 • 46, No. 4, Dec. 1, 2009 (Dec. 1, 2009), pp. 384-386, XP026741568.

Susanne Booth et al: "Comparison of two rapid influenza A/B test kits with reference methods showing high specificity and sensitivity for influenza A infection", Journal of Medical Virology, vol. 78, No. 5, Jan. 1, 2006 (Jan. 1, 2006), pp. 619-622, XP055086842.

BinaxNOW Influenza a and B Test Kit: Kit Product Instructions, 2005. Found online at: https://ensur.invmed. com/ensur/broker/ensurbroker. aspx?code= I N416050&cs=2670349.

USAID, "Avian Influenza Commodities Training Guide", Mar. 1, 2007, XP055176371, [retrieved on Mar. 13, 2015].

Quest Diagnostics—"Instant Testing for Drugs and Alcohol", Jul. 7, 2016, p. 1.

Zaw, Myint et al., "Local Evaluation of a Rapid HIV Assay for Use in Developing Countries", Mar. 1999, 6 pages.

First Examination Report issued in Indian Application No. 394 ELNP 2013 dated Aug. 30, 2017.

* cited by examiner

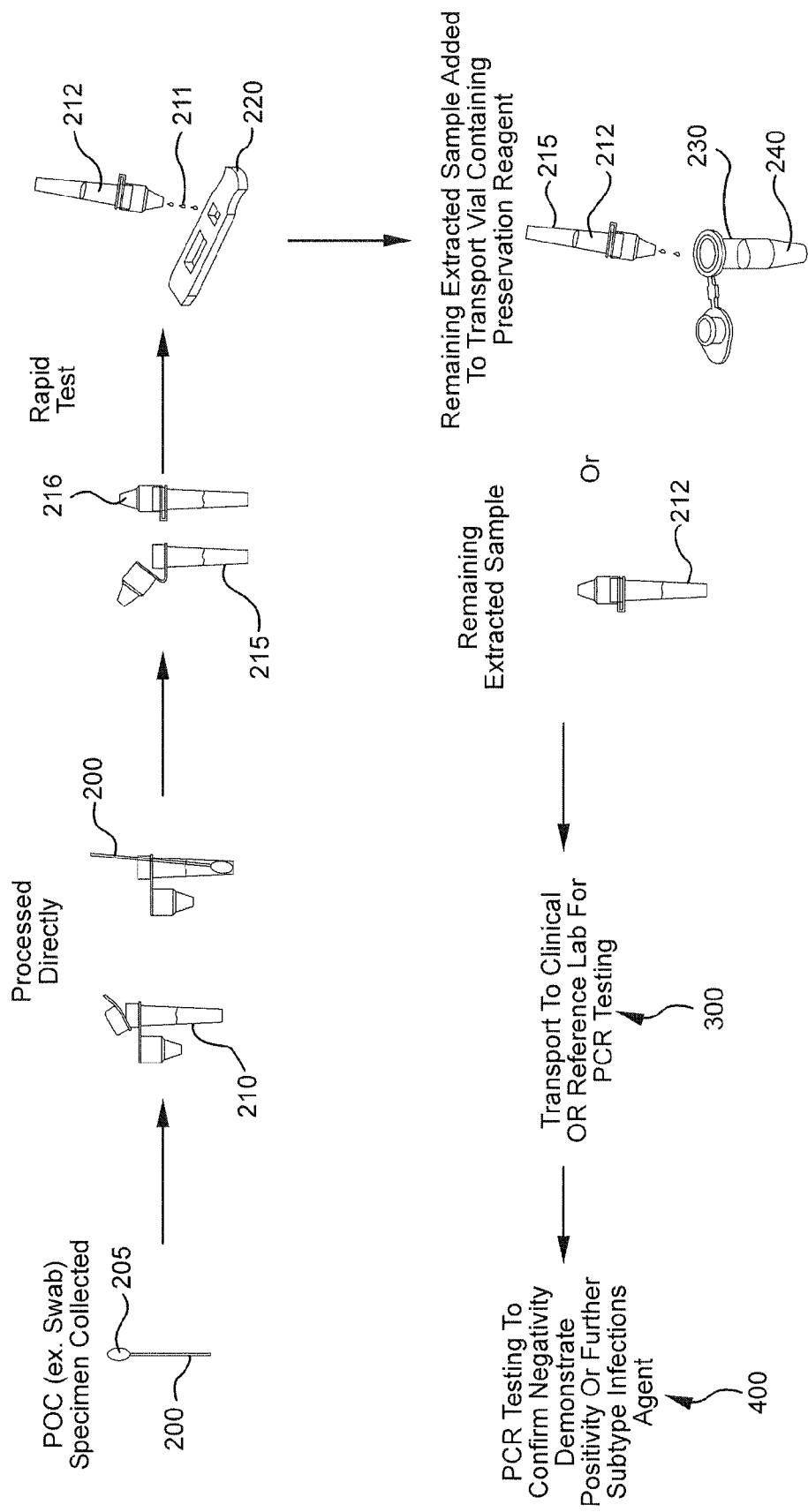

US 9,945,855 B2

METHOD FOR LINKING POINT OF CARE RAPID DIAGNOSTIC TESTING RESULTS TO LABORATORY-BASED METHODS

CROSS REFERENCE TO RELATED APPLICATIONS

This application is a national phase entry under 35 U.S.C. § 371 of International Application No. PCT/US2011/044674 filed Jul. 20, 2011 published in English as International Publication No. WO 2012/012527, which claims the benefit of the filing date of U.S. Provisional Patent Application No. 61/366,076 filed Jul. 20, 2010, the disclosures of which are hereby incorporated herein by reference.

BACKGROUND OF THE INVENTION

The linkage between point of care (POC) rapid testing and laboratory-based testing has typically been addressed through preservation of samples to support culture-based laboratory testing methods. Currently, samples collected at the POC site are either processed and used directly in a rapid test (the portion of the processed sample not used in the rapid test being discarded); or diluted in liquid transport media to enable transfer for laboratory-based testing such as rapid immunoassay, culture and/or polymerase chain reaction (PCR). Specimens that generate negative results from a POC test are often reflex tested—the negative result is confirmed by lab-based testing methods such as PCR. In addition, specimens that generate positive POC test results are frequently tested for additional characterizations such as subtyping or other epidemiologic information.

Referring to FIG. 1, at physician office POC sites (and other non-laboratory sites where patients are seen or samples for rapid testing are collected), swab specimens 100 are used almost exclusively to deliver sample into solution 110 for the rapid test 120. Processing and testing the sample in the physician's office and other non-laboratory sample collection sites does not contemplate a means for enabling lab-based testing such as confirmatory and/or reflex testing or other tests the require lab-based analysis. With the current methods, a physician (or other administrator of a POC rapid test) cannot perform both a POC rapid test and a lab-based test using the sample collected at the site (e.g. the physician's office). Therefore, an opportunity to perform lab-based testing on such samples is lost. Swab samples 130 collected at POC sites within a hospital or clinic are almost exclusively placed within a volume of liquid transport media 140 for transfer to the testing laboratory for remote testing. The diluted samples 150 may be further processed by adding them to a solution 160 for a rapid test 170. However, this method often results in a POC sample diluted 5 to 10-fold, or more, which can diminish performance of the rapid test due to sample dilution effects.

Collection and transport of a second swab at the POC site could be used to address the need to perform laboratory-based testing, although this is clearly not the standard of practice and doubles the number of samples to be taken. In addition, although collected from the same patient, variations in collection methods, organism load, etc. could lead to erroneous results when comparing the test results between two independently collected swab specimens. Accordingly, a system and method that addresses these problems is desired.

SUMMARY OF THE INVENTION

The various embodiments of the present invention enable linkage between POC rapid tests (e.g. immunoassays such as a test for flu virus) and laboratory-based testing (confirmatory testing or other laboratory tests such as diagnostic and identification testing) through the use of a single sample collected and subjected to a rapid test at the POC. The sample (which is any sample that is suspected of containing a target microorganism) is collected and processed under optimal conditions for the particular POC test utilized, ensuring the best possible clinical performance for the POC test (also referred to as a rapid test herein). The sample can be a biological sample collected from a patient and can include any biological fluid or tissue sample including, but not limited to, blood, urine, saliva, and tissue scraped or swabbed from a patient. Samples can also include environmental samples collected in the conventional manner of wiping or swabbing a surface suspected of having the contaminating microorganism. Environmental samples can also include soil samples, air samples, water samples, food samples, etc. Typically, the sample is processed by combining it with a processing reagent compatible with the rapid test. The portion of the sample not used for the rapid test has heretofore been typically discarded. According to one embodiment of the present invention, the remainder of the processed sample is then preserved to allow transfer to a laboratory-based testing environment where confirmatory testing, such as nucleic acid-based testing, can be performed. In other embodiments the remainder is not further diluted, but is still subjected to a laboratory-test. For purposes of the present invention, the site of sample collection and rapid test is referred to as local or POC, while the site for laboratory-based testing is referred to as remote. In the context of the invention, remote simply means removed from the site of sample collection and rapid testing. Remote could vary from very close distances such as different locations in the same building to much larger distances.

The methods described herein can be applied to rapid immunoassays used at POC for rapid diagnosis leading to a critical treatment decision. Rapid immunoassays for use at a POC site are well known and commercially available. They are not described in detail herein. For example, rapid immunoassays are known to detect a wide array of infectious diseases from patient sample including but not limited to influenza testing (e.g. H1N1), RSV testing, Chlamydia trachomatis testing, Neisseria gonorrhea testing, etc.

In another embodiment, samples are collected and first processed directly for use in a rapid immunoassay. The processing step utilizes a rapid test processing reagent and is optimized for producing the maximum clinical performance for the particular immunoassay to be used. This typically involves a relatively gentle lysis treatment in the presence of various salts and detergents. Such lysis reagents are well known and used in conjunction with the commercially available rapid immunoassays and are not described in detail herein. One skilled in the art is aware of the need to select a rapid test processing reagent that will not degrade the sample and make it unsuitable for a contemplated laboratory test.

A portion of the processed sample is then delivered to the POC test device to generate a rapid diagnostic test result. The remainder (or a portion thereof) of the sample is preserved for transfer to a laboratory-based test environment for testing such as confirmatory testing using a molecular diagnostic method. In one embodiment, the molecular diagnostic test is nucleic acid-based. In a preferred embodiment, the nucleic acid-based diagnostic test is PCR.

In another embodiment of the invention, different stabilization transport diluents are utilized to increase stability of the sample. Various formulations are possible where possible constituents include but are not limited to buffers, salts, chelating agents, enzyme inhibitors, nucleic acid binding proteins, chaotropes, etc. One skilled in the art is aware of the suitable constituents and conditions (e.g. pH) for a stabilization transport diluent for a particular application. For example, if the target microorganism in a sample is susceptible to being degraded by a chaotrope, then the skilled person would know not to include chaotropes in the stabilization transport diluent. In certain embodiments of the present invention, the remainder of the processed sample not used for the rapid test may be added to the stabilization transport diluent. In one embodiment, the stabilization transport diluent may already be present in the rapid test processing reagent used for the POC test. In another embodiment, the stabilization transport diluent may be added to the remainder of the processed sample after a portion of the sample has been removed and used for the rapid immunoassay. In a preferred embodiment, the stabilization transfer diluent stabilizes nucleic acids in the sample.

BRIEF DESCRIPTION OF THE DRAWINGS

FIG. 1B illustrates the method for POC and lab-based testing of the present invention.

DETAILED DESCRIPTION OF PREFERRED EMBODIMENTS

Figure 1A:
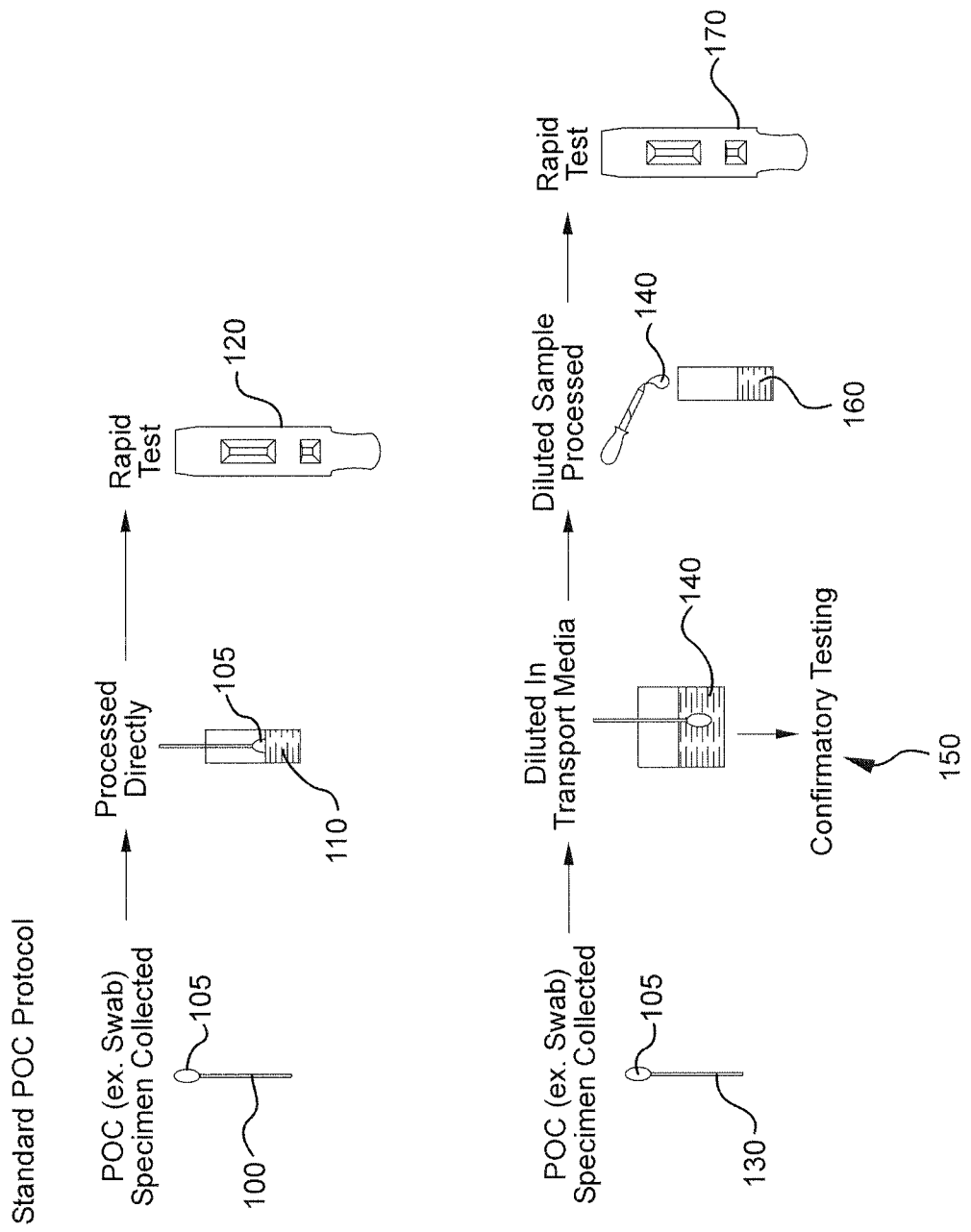
FIG. 1A illustrates the prior art method for the standard protocol for POC and lab-based testing.

FIG. 1A illustrates the current standard protocol for POC and lab-based testing. A specimen 105 is collected, for example, using a swab 100. Other conventional implements for collecting biological samples are contemplated for use herein. Such implements, such as a scraper or spatula are not described in detail herein and are well known to those skilled in the art. Specimen 105 is then processed directly by placing swab 100 with sample 105 in solution 110 for POC rapid testing 120. In this situation, any remaining sample is discarded and a new sample must be collected for additional lab-based testing such as confirmatory testing or reflex testing. In the alternative standard protocol, specimen 105 on swab 130 is first diluted in transport media 140. A portion of the diluted transport media 140 containing specimen 105 is further processed in solution 160 for POC testing 170. In this situation, processed specimen 105 is diluted to a level that diminishes the results of POC testing 170 as illustrated in Example 1 below. The remaining portion in the diluent is used for laboratory testing 150, such as subtyping and reflex testing.

FIG. 1B illustrates one embodiment of the method for POC and laboratory testing of the present invention. Specimen 205 is collected on swab 200 and processed directly using a rapid test processing reagent 210 that is optimized for producing the maximum clinical performance for the particular immunoassay. The swab 200 is removed and the rapid test container 215 is closed with dispenser lid 216. The capped test container 215 with dispenser lid 216 is used to dispense a portion of processed sample 211 onto rapid test strip 220. Rapid POC testing 220 is performed using a portion of the specimen 211 processed in the rapid test processing reagent. The remaining portion 212 of the processed sample after POC testing is transported 300 to the clinical lab for laboratory testing 400. In the alternative, the remaining portion 212 of the processed sample after POC testing is added to transport vial 230 that contains stabilization transport diluent 240. The stabilization transport diluent is designed to help maintain the integrity of the sample. In this regard, various formulations are possible depending upon a variety of factors including the stability of the target microorganism, the type of laboratory test contemplated, and the constituents of the rapid test reagent. Considering these factors, the skilled person will select conditions (e.g. optimal pH conditions) and constituents (e.g. buffer types, salts, chelating agents, enzyme inhibitors, nucleic acid binding proteins, chaotropes, etc.) for the stabilization transport diluent. The stabilized sample is then transported to the clinical lab 300 for confirmatory or other laboratory testing 400. This embodiment illustrates how one sample, specimen 205, can be processed at the POC site for both POC testing and lab-based testing. This embodiment also demonstrates that a sample processed in conditions optimal for POC testing can be used for lab-based testing.

There are a variety of rapid tests that are currently commercially available. Such rapid tests are not described in detail herein, but are available from a variety of sources including Becton Dickinson, Alere, Quidel, Meridian, Genzyme, etc. The invention is not limited to use with a particular rapid test.

EXAMPLES

The following examples illustrate various embodiments of the invention and are not meant to limit the invention except in a manner consistent with the claims presented herein.

Example 1

The ability to detect influenza viral RNA in samples processed for use in a POC rapid immunoassay was demonstrated using an H1N1 positive clinical specimen collected by upper nasal swab from an individual exhibiting positive flu symptoms. The swab was placed in 3 ml of commercially available transport media (BD™ Universal Viral Transport Media available from Becton Dickinson) and confirmation that the sample tested positive for H1N1 was obtained. For testing, certain 50 µl aliquots of that specimen were obtained. One aliquot was mixed directly with a rapid test processing reagent for the immunoassay and others were further diluted (5×, 25×, 125× or 625×) with stabilization transport diluent prior to mixing with the rapid test processing reagent. Each 50 µl aliquot of sample was combined with 25 µl of rapid test processing reagent. The rapid test processing reagent (tris buffer, NaCl, 6% detergent and pH adjusted to 8.0) was optimized to release and preserve the influenza nucleoprotein which is the target antigen for the rapid immunoassay. The immunoassay testing results on the various sample dilutions are shown in Table 1.

TABLE 1

Immunoassay Results

| H1N1 Clinical Sample | Rapid Immunoassay Result |
| --- | --- |
| undiluted | Flu A positive/Flu B negative |
| 1:5 dilution | Flu A positive/Flu B negative |
| 1:25 dilution | Flu A negative/Flu B negative |
| 1:125 dilution | Flu A negative/Flu B negative |
| 1:625 dilution | Flu A negative/Flu B negative |

The immunoassay test results in Table 1 demonstrate the effect of specimen dilution on rapid test performance. Samples diluted greater than 1:5 resulted in a negative rapid immunoassay test. In order to provide optimal POC clinical performance, specimen dilution should therefore be minimized or avoided. Dilution of the specimen (excluding the initial placement of the sample into solution) greater than 1:5 diminishes the possibility of detection with a rapid immunoassay test. The use of direct swab processing in the POC setting enhances the clinical performance of rapid immunoassays. However, standard POC testing methods using direct swab samples, as noted above, do not enable lab-based testing because of initial placement of such samples into a transport diluent.

Example 2

Figure 2A:
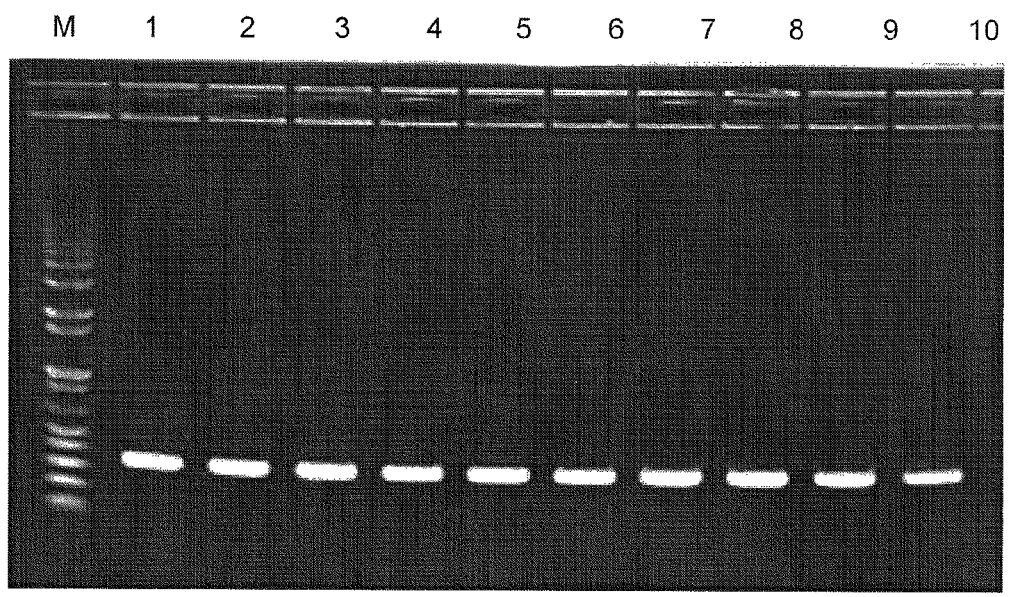
FIG. 2A/B demonstrates the results from RT-PCR for Influenza A from samples processed for POC testing under various dilution conditions.
Figure 2B:
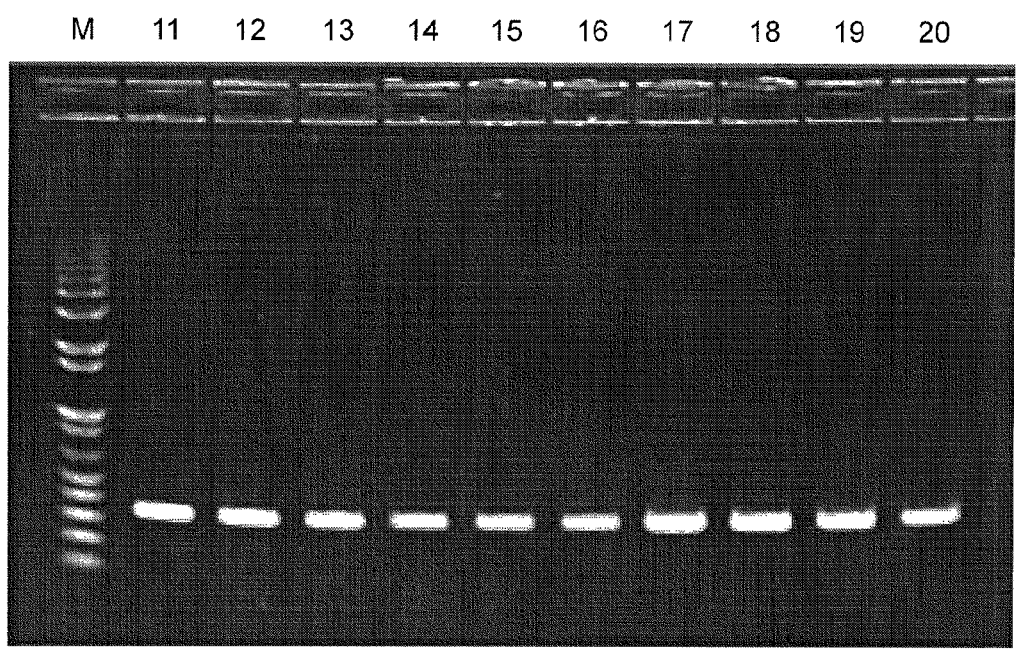

Aliquots (50 µl) of each dilution prepared in Example 1 were mixed with 25 µl rapid test processing reagent. One set of processed samples was stored at room temperature (RT) for 5 minutes prior to RNA extraction using a Qiagen Viral RNA miniprep kit according to the manufacturer's instructions. Additional sets of processed samples were stored for 4 hours at either 4° C. or RT prior to RNA extraction. A 5 µl portion of the extracted RNA samples was then used as target for reverse transcription-polymerase chain reaction (RT-PCR) with primers specific for the matrix gene of influenza A virus. The RT-PCR results are shown in FIGS. 2A and 2B. Tables 2 and 3 show the processing conditions corresponding to each lane of the agarose gel of the RT-PCR results shown in FIGS. 2A and 2B.

TABLE 2

Lanes of Agarose Gel of FIG. 2A

| Processing Method | Lane on Agarose Gel |
| --- | --- |
| Molecular Weight Marker | M |
| Sample diluted 1:5, processed for rapid test, RNA extraction immediately | 1 |
| Sample diluted 1:5, processed for rapid test, stored at 4° C. for 4 hrs before RNA extraction | 2 |
| Sample diluted 1:5, processed for rapid test, stored at Room Temperature for 4 hrs before RNA extraction | 3 |
| Sample diluted 1:25, processed for rapid test, RNA extraction immediately | 4 |
| Sample diluted 1:25, processed for rapid test, stored at 4° C. for 4 hrs before RNA extraction | 5 |
| Sample diluted 1:25, processed for rapid test, stored at Room Temperature for 4 hrs before RNA extraction | 6 |
| Sample diluted 1:5, RNA extraction (no rapid test/no rapid test reagent) | 7 |
| Sample diluted 1:25, RNA extraction (no rapid test/no rapid test reagent) | 8 |
| Sample diluted 1:125, RNA extraction (no rapid test/no rapid test reagent) | 9 |
| Sample diluted 1:625, RNA extraction (no rapid test/no rapid test reagent) | 10 |

TABLE 3

Lanes of Agarose Gel of FIG. 2B

| Processing Method | Lane on Agarose Gel |
| --- | --- |
| Molecular Weight Marker | M |
| Sample diluted 1:125, processed for rapid test, RNA extraction immediately | 11 |
| Sample diluted 1:125, processed for rapid test, stored at 4° C. for 4 hrs before RNA extraction | 12 |
| Sample diluted 1:125, processed for rapid test, stored at Room Temperature for 4 hrs before RNA extraction | 13 |
| Sample diluted 1:625, processed for rapid test, RNA extraction immediately | 14 |
| Sample diluted 1:625, processed for rapid test, stored at 4° C. for 4 hrs before RNA extraction | 15 |
| Sample diluted 1:625, processed for rapid test, stored at Room Temperature for 4 hrs before RNA extraction | 16 |
| Sample diluted 1:5, RNA extraction (no rapid test/no rapid test reagent) | 17 |
| Sample diluted 1:25, RNA extraction (no rapid test/no rapid test reagent) | 18 |
| Sample diluted 1:125, RNA extraction (no rapid test/no rapid test reagent) | 19 |
| Sample diluted 1:625, RNA extraction (no rapid test/no rapid test reagent) | 20 |

FIGS. 2A and 2B demonstrate that samples processed for rapid immunoassay testing could also be used for RNA extraction, which enabled lab-based PCR testing to be performed. RNA was extracted from samples diluted well below the limit of detection for the rapid test, indicating that even small amounts of viral RNA remained stable in the processed sample. Storage of the processed samples at 4° C. or room temperature for up to four hours before RNA extraction also indicates the viral nucleic acid remained stable after processing. Comparison of PCR test results using RNA isolated from the processed samples to RNA extracted directly from the sample dilutions (lanes 7-10, 17-20) demonstrated that the integrity of the viral RNA was minimally affected by the processing step for the rapid test.

Example 3

Figure 3:
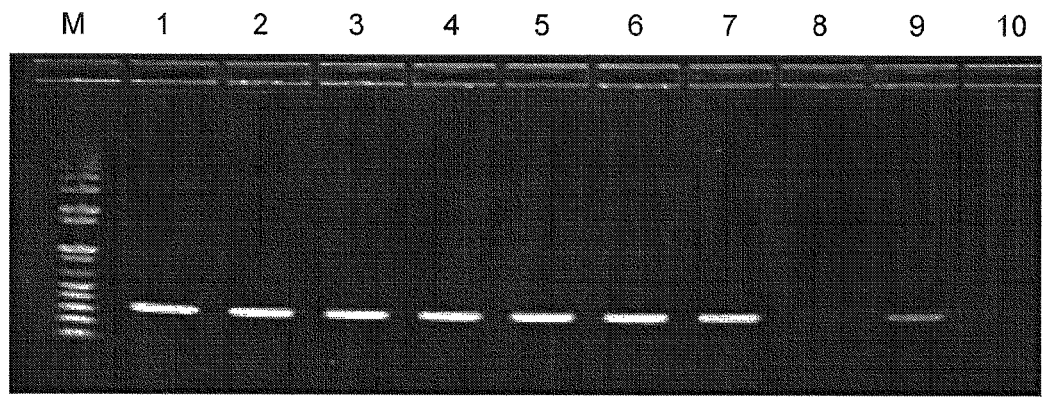
FIG. 3 demonstrates the results from RT-PCR for Influenza A from samples processed for POC testing using two different rapid test processing reagents and various storage conditions using the method of the present invention.

The stability of viral RNA in processed samples was examined using two different rapid test processing reagents optimized for use in the rapid immunoassay for influenza A/B. Sample processing for rapid immunoassays typically involves the use of a relatively gentle lysis treatment mediated by a reagent containing various salts and detergents. Two different formulations for the rapid test processing reagent were examined for compatibility with the described method. Formulation A contained Tris buffer, NaCl, 16% detergent at a pH of 7.8. Formulation B contained Tris buffer, NaCl, 6% detergent at a pH of 8.0. Aliquots of an H1N1 positive clinical specimen described in Example 1 were processed with both formulations, and the processed samples were used immediately for RNA extraction using the Qiagen Viral RNA miniprep kit, or stored at RT and 4° C. for up to 24 hours prior to RNA extraction. A portion of the extracted RNA samples was then used as target for RT-PCR with primers specific for the matrix gene of the influenza A virus. The RT-PCR results are shown in FIG. 3. Table 4 shows the processing conditions corresponding to each lane of the agarose gel of the RT-PCR results shown in FIG. 3.

TABLE 4

Lanes of Agarose Gel of FIG. 3.

| Processing Method | Lane on Agarose Gel |
| --- | --- |
| Molecular Weight Marker | M |
| Sample processed with rapid test processing reagent A, RNA extraction immediately | 1 |
| Sample processed with rapid test processing reagent A, stored at 4° C. for 4 hrs before RNA extraction | 2 |
| Sample processed with rapid test processing reagent A, stored at 4° C. for 24 hrs before RNA extraction | 3 |
| Sample processed with rapid test processing reagent B, RNA extraction immediately | 4 |
| Sample processed with rapid test processing reagent B, stored at 4° C. for 4 hrs before RNA extraction | 5 |
| Sample processed with rapid test processing reagent B, stored at 4° C. for 24 hrs before RNA extraction | 6 |
| Sample processed with rapid test processing reagent A, stored at room temperature for 4 hrs before RNA extraction | 7 |
| Sample processed with rapid test processing reagent A, stored at room temperature for 24 hrs before RNA extraction | 8 |
| Sample processed with rapid test processing reagent B, stored at room temperature for 4 hrs before RNA extraction | 9 |
| Sample processed with rapid test processing reagent B, stored at room temperature for 24 hrs before RNA extraction | 10 |

FIG. 3 demonstrates both formulation A and formulation B are compatible with use of the processed sample for RNA extraction and PCR testing. Storage of the processed samples at 4° C. for up to 24 hours prior to RNA extraction suggests little degradation of the viral RNA occurred in samples processed with either formulation. However, prolonged storage of the extracted samples at RT demonstrated decreased PCR performance, possibly due to viral RNA degradation over time (lanes 8, 10).

Example 4

Figure 4:
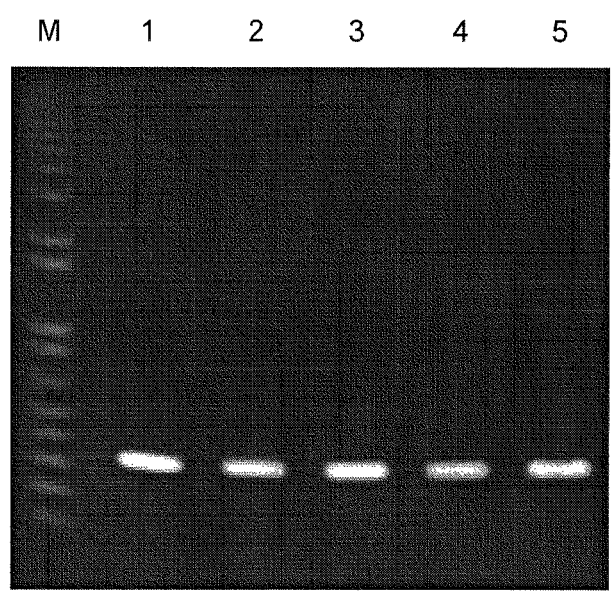
FIG. 4 demonstrates the results from RT-PCR for Influenza A from samples processed for POC testing and then mixed with two different stabilization transport diluents and various storage conditions using the method of the present invention.

Two potential stabilization transport diluents were examined in an attempt to increase stability of viral RNA in samples processed for POC testing. The stabilization transport diluent was designed to help maintain the integrity of nucleic acids present in the sample. Various formulations are possible where optimal pH conditions, buffer types, salts, chelating agents, enzyme inhibitors, nucleic acid binding proteins, chaotropes, etc. may be employed. Stabilization transport diluent A contained Qiagen viral RNA lysis/binding buffer. Stabilization transport diluent B contained 6 M guanidine thiocyanate+20 mM EDTA. Aliquots of an H1N1 positive clinical specimen were processed using rapid test processing reagent B. The processed samples were immediately used for RNA extraction or mixed with one of the two different stabilization transport diluents and stored at 4° C. for up to six days prior to RNA extraction. A portion of the extracted RNA samples was then used as target for RT-PCR with primers specific for the matrix gene of the influenza A virus. The RT-PCR results are shown in FIG. 4. Table 5 shows the processing conditions corresponding to each lane of the agarose gel of the RT-PCR results shown in FIG. 4.

TABLE 5

Lanes of Agarose Gel of FIG. 4.

| Processing Method | Lane on Agarose Gel |
| --- | --- |
| Molecular Weight Marker | M |
| Sample processed for rapid test, RNA extraction immediately | 1 |
| Sample processed for rapid test, mixed with stabilization transport | 2 |

TABLE 5-continued

Lanes of Agarose Gel of FIG. 4.

| Processing Method | Lane on Agarose Gel |
|---|---|
| diluent A, stored at 4° C. for 3 days before RNA extraction | |
| Sample processed for rapid test, mixed with stabilization transport diluent B, stored at 4° C. for 3 days before RNA extraction | 3 |
| Sample processed for rapid test, mixed with stabilization transport diluent A, stored at 4° C. for 6 days before RNA extraction | 4 |
| Sample processed for rapid test, mixed with stabilization transport diluent B, stored at 4° C. for 6 days before RNA extraction | 5 |

Using either formulation of the stabilization transport diluent, intact viral RNA was extracted from samples processed for POC testing that had been stored for up to 6 days at 4° C. Comparing the PCR results from the stored samples (lanes 2-5) to those obtained using RNA extracted immediately after processing (lane 1) suggest little, if any, degradation of the viral RNA occurred over time in the processed samples treated with either stabilization transport diluent.

Example 5

Figure 5:
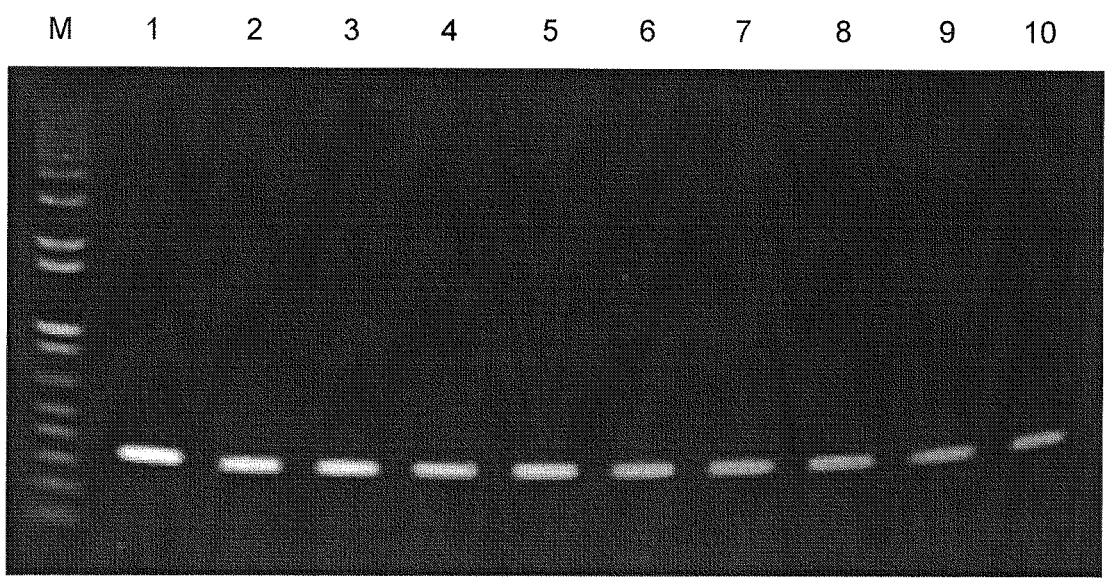
FIG. 5 demonstrates the results from RT-PCR for Influenza A from samples processed for POC testing and then mixed with a stabilization transport diluent and various storage conditions using the method of the present invention.

A stabilization transport diluent was used in an attempt to increase stability of the viral RNA in samples processed for POC testing, particularly when samples are stored for extended periods of time at room temperature. Aliquots of an H1N1 positive clinical specimen were processed using rapid test processing reagent formulation B described in Example 3, and the processed samples were immediately used for RNA extraction, or mixed with stabilization transport diluent A and stored at RT and 4° C. for up to seven days prior to RNA extraction. A portion of the extracted RNA samples was then used as target for RT-PCR with primers specific for the matrix gene of the influenza A virus. The PCR results are shown in FIG. 5. Table 6 shows the processing conditions corresponding to each lane of the agarose gel of the RT-PCR results shown in FIG. 5.

TABLE 6

Lanes of Agarose Gel of FIG. 5.

| Processing Method | Lane on Agarose Gel |
|---|---|
| Molecular Weight Marker | M |
| Sample processed for rapid test, RNA extraction immediately | 1 |
| Sample processed for rapid test, mixed with stabilization transport diluent, stored at 4° C. for 3 days before RNA extraction | 2 |
| Sample processed for rapid test, mixed with stabilization transport diluent, stored at 4° C. for 4 days before RNA extraction | 3 |

TABLE 6-continued

Lanes of Agarose Gel of FIG. 5.

| Processing Method | Lane on Agarose Gel |
|---|---|
| Sample processed for rapid test, mixed with stabilization transport diluent, stored at 4° C. for 5 days before RNA extraction | 4 |
| Sample processed for rapid test, mixed with stabilization transport diluent, stored at 4° C. for 6 days before RNA extraction | 5 |
| Sample processed for rapid test, mixed with stabilization transport diluent, stored at 4° C. for 7 days before RNA extraction | 6 |
| Sample processed for rapid test, mixed with stabilization transport diluent, stored at room temperature for 1 day before RNA extraction | 7 |
| Sample processed for rapid test, mixed with stabilization transport diluent, stored at room temperature for 2 days before RNA extraction | 8 |
| Sample processed for rapid test, mixed with stabilization transport diluent, stored at room temperature for 3 days before RNA extraction | 9 |
| Sample processed for rapid test, mixed with stabilization transport diluent, stored at room temperature for 4 days before RNA extraction | 10 |

Mixing the processed sample with a stabilization transport diluent increased the stability of the viral nucleic acid, and enabled longer-term storage and transport of the processed sample at various temperatures. FIG. 5 demonstrates that intact viral RNA can be extracted from processed samples mixed with the stabilization transport diluent after storage of the samples for up to 7 days at 4° C. or up to 4 days at room temperature.

Example 6

Figure 6A:
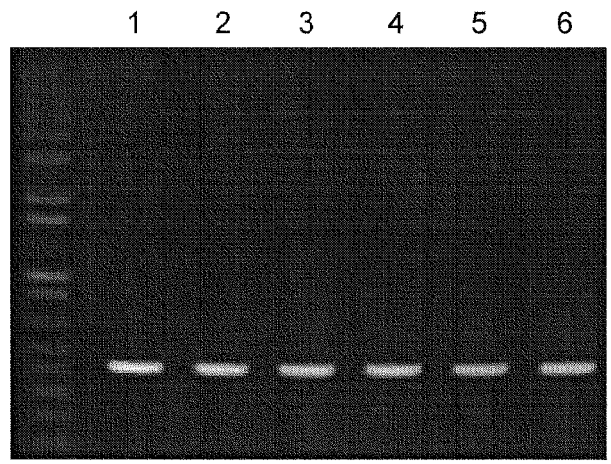
FIG. 6A-C demonstrate the results from RT-PCR for two strains of Influenza A and one strain of Influenza B under various storage conditions using the method of the present invention.
Figure 6B:
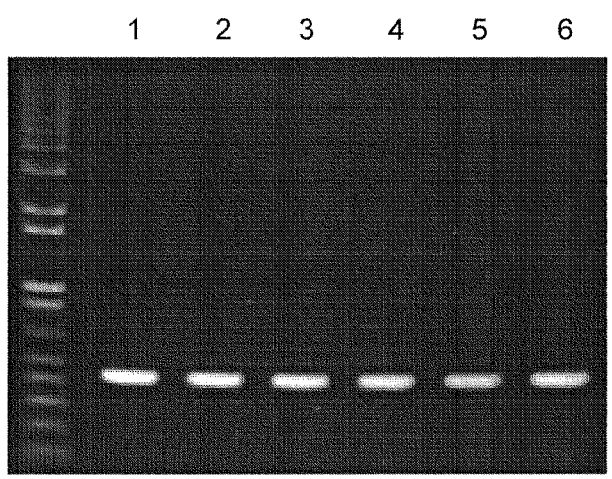
Figure 6C:
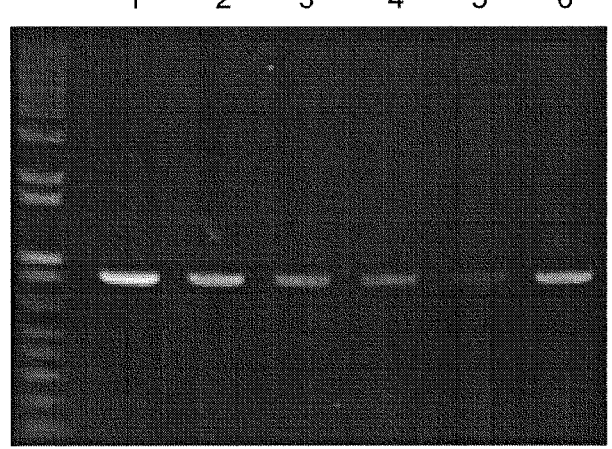

Stabilization transport diluent B was used to examine stabilization properties across different influenza strains: A: Influenza A strain A/Solomon Island/03/06 (H1N1); B: Influenza A strain A/Wisconsin/67/2005 (H3N2); and C: Influenza B strain B/Jiangsu/10/2003. Aliquots (50 µl) of cell culture supernatants from cultures into which virus had been introduced from nasal swabs of a patient exhibiting symptoms of influenza and these aliquots were combined with rapid test processing reagent B (25 µl) and the processed samples were either immediately used for RNA extraction, or mixed with stabilization transport diluent B (75 µl) and stored at 4° C. or −20° C. for up to fourteen days prior to RNA extraction. A portion of the extracted RNA samples was then used as target for RT-PCR reactions with primers specific for the matrix gene of influenza A or the nucleoprotein gene of influenza B. The PCR results are shown in FIG. 6. Table 7 shows the processing conditions corresponding to each lane of the agarose gel of the RT-PCR results shown in FIG. 6.

TABLE 7

Table 6: Lanes of Agarose Gel of FIG. 6.

| Processing Method | Lane on Agarose Gel |
|---|---|
| Sample processed for rapid test, RNA extraction immediately | 1 |
| Sample processed for rapid test, mixed with stabilization transport diluents B, stored at 4° C. for 2 days before RNA extraction | 2 |
| Sample processed for rapid test, mixed with stabilization transport diluents B, stored at 4° C. for 7 days before RNA extraction | 3 |
| Sample processed for rapid test, mixed with stabilization transport diluents B, stored at 4° C. for 10 days before RNA extraction | 4 |
| Sample processed for rapid test, mixed with stabilization transport diluents B, stored at 4° C. for 14 days before RNA extraction | 5 |
| Sample processed for rapid test, mixed with stabilization transport diluents B, stored at −20° C. for 7 days before RNA extraction | 6 |

Mixing the processed sample with a stabilization transport diluent increased the stability of the viral nucleic acid in all three strains of Influenza for up to 14 days at 4° C. or up to 7 days at −20° C. FIG. 6 demonstrates that intact viral RNA from various strains can be extracted from processed samples mixed with the stabilization transport diluent after storage of the samples for up to 7 days at 4° C. or up to 14 days at −20° C. For both the A and B strains, intact viral RNA was extracted after storage under all conditions.

Example 7

Utility of one embodiment of the method of the present invention illustrated in FIG. 1B was demonstrated in a clinical trial performed during the 2010-2011 influenza season. Paired nasopharyngeal (NPS) or upper nasal swabs (NS) were collected from patients enrolled in the POC influenza study. One swab was processed directly for use in an investigational rapid immunoassay at the POC site and then a portion (3 to 5 drops) of the remaining sample was mixed with the stabilization transport diluent B (200 µl) and stored at either 2 to 8° C. for up to 5 days or −20° C. for up to two weeks prior to being sent to a laboratory for PCR analysis. The second swab was placed in 3 ml of viral transport media and sent directly to a clinical laboratory for PCR testing.

All PCR testing was performed using the Prodesse Pro-Flu+ assay available from GenProbe, Inc. (San Diego, Calif.). The Prodesse ProFlu+ test is FDA-cleared and is able to detect and differentiate Influenza A, Influenza B, and RSV in respiratory specimens. For the swab-in-transport media specimens, RNA was extracted using the NucliSENS easyMAG System (bioMérieux) according to the Prodesse ProFlu+ package insert. For the POC processed samples in the stabilization transport diluent, RNA was extracted using the Qiagen Viral RNA miniprep kit according to the manufacturer. Five microliters of extracted RNA was used for PCR amplification using a Cepheid SmartCycler II instrument according to the assay procedure described in the Prodesse ProFlu+ package insert. Interpretation of PCR results for specimens and controls was determined using the Cepheid SmartCycler Dx software according to the protocols outlined in the Prodesse ProFlu+ package insert. The positive and negative percent agreement between results obtained from the POC stabilized sample (POC PCR) and the swab-in-transport media sample (Reference PCR) are shown below in Table 7.

TABLE 7

Comparison of PCR results from POC processed samples compared to Reference PCR

| | Influenza A | | | | Influenza B | | | | RSV | | |
|---|---|---|---|---|---|---|---|---|---|---|---|
| | Reference PCR | | | | Reference PCR | | | | Reference PCR | | |
| POC PCR | P | N | | POC PCR | P | N | | POC PCR | P | N | |
| P | 150 | 22 | 172 | P | 91 | 12 | 103 | P | 18 | 2 | 20 |
| N | 5 | 335 | 340 | N | 8 | 401 | 409 | N | 1 | 491 | 492 |
| | 155 | 357 | 512 | | 99 | 413 | 512 | | 19 | 493 | 512 |
| Reference Method: PCR from swab in transport media Positive Percent Agreement: 96.8% Negative Percent Agreement: 93.8% | | | | Reference Method: PCR from swab in transport media Positive Percent Agreement: 91.9% Negative Percent Agreement: 97.1% | | | | Reference Method: PCR from swab in transport media Positive Percent Agreement: 94.7% Negative Percent Agreement: 99.6% | | | |

Table 7 demonstrates that samples can be processed for rapid POC testing and a portion of that processed sample can be used for lab-based testing such as PCR. Greater than 91.9% agreement was obtained in various viral strains when comparing a sample that was directly processed for PCR to a sample that was first processed under conditions optimal for rapid POC testing and then subsequently processed for PCR.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A method for using a sample initially collected at the point of care (POC) as source for sample for use in a laboratory that is not at the point of care (POC) comprising:
   a) collecting a sample suspected of containing a target microorganism for a POC test, wherein the POC test is an immunoassay;
   b) preparing the collected sample for use in the POC test by combining the collected sample with a POC processing reagent configured for use with a POC test, wherein the POC processing reagent consists essentially of a gentle lysis reagent that consists of a Tris buffer, NaCl, and a detergent, and wherein the gentle lysis reagent has a pH of 7.8 to 8, and wherein the collected sample is not combined with any additional reagents thereafter prior to the POC test;
   c) using only a portion of the processed sample for the POC test leaving a remaining portion not used for the POC test; and
   d) using at least a portion of the remaining portion of the processed sample for a laboratory test.

2. The method of claim 1, wherein an implement is used to collect the sample and the implement is selected from the group consisting of a scraper and a swab.

3. The method of claim 1, wherein a location for the POC test is a physician's office.

4. The method of claim 1, wherein, after a portion of the processed sample has been removed for use in the POC test, the at least a portion of the remaining portion of the processed sample and a stabilization transport diluent are combined together in a transport container for sample stabilization during transport to the laboratory test.

5. The method of claim 4, wherein the stabilization transport diluent stabilizes nucleic acids in the processed sample and comprises at least one buffer and at least one salt.

6. The method of claim 1, after a portion of the processed sample has been removed for use in the POC test, the at least a portion of the remaining portion of the processed sample is not combined with a stabilization transport diluent for sample stabilization during transport to the laboratory test.

7. The method of claim 5, wherein the laboratory test is subtyping based upon a nucleic acid assay.

8. The method of claim 1, wherein the laboratory test is reflex testing.

9. The method of claim 5, wherein the laboratory test is a nucleic acid assay.

10. The method of claim 9, wherein the nucleic acid assay is polymerase chain reaction (PCR).

11. The method of claim 4, wherein the stabilization transport diluent is added to a container containing at least a portion of the remaining portion of the processed sample.

12. The method of claim 4, wherein at least a portion of the remaining portion of the processed sample is added to a container containing the stabilization transport diluent.

13. The method of claim 1, wherein the sample suspected of containing a target microorganism is selected from the group consisting of a biological sample and an environmental sample.

14. A method for using a single sample suspected of containing a target microorganism initially collected at the point of care (POC) for both a POC test immunoassay and a laboratory test not conducted at the POC comprising:
   a) collecting a sample for a POC test;
   b) processing the sample for the POC test by combining the collected sample with a POC processing reagent, wherein the POC processing reagent consists essentially of a gentle lysis reagent that consists of a Tris buffer, NaCl, and a detergent, and wherein the gentle lysis reagent has a pH of 7.8 to 8;
   c) selecting the POC test;
   d) using only a portion of the processed sample for the POC test wherein the processed sample is not combined with other processing reagents prior to the POC test, leaving a remaining portion of the processed sample;
   e) combining, in a container, at least a portion of the remaining portion of the processed sample and a stabilization transport diluent that stabilizes at least nucleic acids in the portion of the processed sample combined with the stabilization transport diluent;
   f) transferring the container containing the combined remaining portion of the processed sample and stabilization transport diluent to a laboratory not at the POC for laboratory testing; and
   g) using the combined remaining portion of the processed sample combined and stabilization transport diluent for reflex testing or subtyping using PCR.

15. The method of claim 14, wherein an implement is used to collect the sample and the implement is selected from the group consisting of a scraper and a swab.

16. The method of claim 14, wherein a location for the POC test is a physician's office.

17. The method of claim 14, wherein the stabilization transport diluent stabilizes nucleic acids in the processed sample and comprises at least one buffer and at least one salt.

18. The method of claim 14, wherein the sample suspected of containing a target microorganism is selected from the group consisting of a biological sample and an environmental sample.

* * * * *